United States Patent
Bertrand et al.

(10) Patent No.: US 12,251,113 B2
(45) Date of Patent: Mar. 18, 2025

(54) METHOD AND APPARATUS FOR ADJUSTABLE AND SIMULTANEOUS MULTIPLE VESSEL COMPRESSION

(71) Applicant: LES ENTREPRISES NANOSTENT INC., Quebec (CA)

(72) Inventors: Olivier François Bertrand, Quebec (CA); Ramses Galaz, Hermosillo (MX); Arnoldo Heredia, Miramar (MX); Daniel Gomez, Hermosillo (MX)

(73) Assignee: LES ENTREPRISES NANOSTENT INC., Quebec (CA)

( * ) Notice: Subject to any disclaimer, the term of this patent is extended or adjusted under 35 U.S.C. 154(b) by 613 days.

(21) Appl. No.: 17/614,015

(22) PCT Filed: Jun. 1, 2020

(86) PCT No.: PCT/CA2020/050751
§ 371 (c)(1),
(2) Date: Nov. 24, 2021

(87) PCT Pub. No.: WO2020/243825
PCT Pub. Date: Dec. 10, 2020

(65) Prior Publication Data
US 2022/0233201 A1    Jul. 28, 2022

Related U.S. Application Data

(60) Provisional application No. 62/858,064, filed on Jun. 6, 2019.

(51) Int. Cl.
*A61B 17/132*    (2006.01)
*A61B 17/00*    (2006.01)

(52) U.S. Cl.
CPC ...... *A61B 17/1325* (2013.01); *A61B 17/1327* (2013.01); *A61B 2017/00902* (2013.01)

(58) Field of Classification Search
CPC ............ A61B 17/1325; A61B 17/1327; A61B 2017/00902; A61B 2017/00893; A61B 2017/12004
See application file for complete search history.

(56) References Cited

U.S. PATENT DOCUMENTS 5,728,120 A    3/1998    Shani et al.
8,556,928 B2   10/2013   Bao et al.
(Continued)

FOREIGN PATENT DOCUMENTS

CN    102076272    5/2011
EP    3432809      2/2022
(Continued)

OTHER PUBLICATIONS

European Search Report, 8 pages, Nemchand Jaya, Jul. 7, 2022.
International Search Report, 3 pages, Jason Jarjoura, Aug. 11, 2020.

*Primary Examiner* — Julian W Woo
(74) *Attorney, Agent, or Firm* — Benoit&Cote Inc.; Charles-Andre Caron; Irina Kostko

(57) ABSTRACT

A device for applying an adjustable and simultaneous compression on vessel access points. The device comprises a frame comprising a body with at least two cavities through the body to be placed about surfaces of a patient corresponding to the at least two cavities. At least two compression members are movably fitted in the cavities, wherein a portion of the frame defines a space into which a portion of the compression member is fitted and around which it hinges. A side of the compression members opposite a portion around which it hinges comprises a locking mechanism which releasably engages with the frame at an interface between said side and the frame to lock each one of the at (Continued)

least two compression members in a given hinge position for applying the pressure onto the vessel access point depending on the hinge position.

17 Claims, 15 Drawing Sheets

(56) References Cited

U.S. PATENT DOCUMENTS

| | | |
|---|---|---|
| 8,777,982 B2 | 7/2014 | Clark |
| 9,510,838 B2 | 12/2016 | Pancholy |
| 9,642,628 B2 | 5/2017 | Pancholy et al. |
| 11,207,076 B2 * | 12/2021 | Clark .................. A61B 17/132 |
| 2013/0237866 A1 | 9/2013 | Cohen et al. |
| 2017/0181882 A1 | 6/2017 | Chisena et al. |
| 2018/0008280 A1 | 1/2018 | Clark |
| 2018/0008282 A1 | 1/2018 | Hazama et al. |

FOREIGN PATENT DOCUMENTS

| | | |
|---|---|---|
| JP | 2013176557 | 3/2016 |
| JP | 2018522706 | 4/2021 |
| KR | 10-2018-0037190 | 4/2018 |
| WO | 2017023499 | 2/2017 |

* cited by examiner

METHOD AND APPARATUS FOR ADJUSTABLE AND SIMULTANEOUS MULTIPLE VESSEL COMPRESSION

CROSS-REFERENCE TO RELATED APPLICATIONS

This application claims benefit or priority of U.S. provisional patent application 62/858,064, filed Jun. 6, 2019, which is hereby incorporated herein by reference in its entirety.

BACKGROUND

(a) Field

The subject matter disclosed generally relates to devices used during transradial catheterization or interventions. More specifically, it relates to a device for applying an adjustable and simultaneous compression on vessel access points.

(b) Related Prior Art

Although the standard access site to perform diagnostic angiography and percutaneous interventions for coronary or peripheral vessels has been the femoral artery, the use of radial or ulnar artery (arteries from the wrist) has become more popular over the last decade. Indeed, the superficial nature of those vessels as well as their reduced sizes confer significant benefits compared to the much larger and deeper femoral artery. Indeed, after removal of equipment introduced into the vessels such as sheaths and catheters, hemostasis can be obtained by maintaining some pressure over the puncture site. Hence, the risks of vascular complications and access-site bleeding are much reduced with wrist vascular access compared to femoral access.

However, one specific caveat or complication of using the wrist approach either through the radial or ulnar artery is that the vessel might occlude during the hemostasis period, hence the anterograde flow can be transiently or permanently interrupted. In the large majority of cases, this occlusion will remain asymptomatic since there is a dual or triple arterial system which provides flow to the hand and fingers.

There are several methods which can be used to reduce the risks of radial artery occlusion (RAO) after transradial catheterization or interventions. These can be broadly described as pharmacologic and non-pharmacologic methods. The pharmacologic method relies on administering to patient anticoagulant such as unfractioned heparin, low molecular weight heparin, bivalirudin or similar agent at the beginning of the procedure. The patient being anticoagulated, there is less risk of RAO during compression of the vessel until hemostasis is completed. The other most important non-pharmacologic parameter which might influence the risks of peri-procedural RAO is the size of the sheaths and catheters that the operator uses to perform either a diagnostic angiography procedure or an intervention with balloons and/or stent implantation. Indeed, larger sheath/artery ratio has been clearly associated with higher risks of peri-procedural RAO. Hence, transradial procedures performed with 5Fr sheaths and catheters have less risks of RAO than procedures using 6Fr sheaths and catheters.

The incidence of RAO is highly variable and rates between 0% and 33% at hospital discharge or within 24 h of procedures have been reported. Furthermore, it should be noted that spontaneous vessel recanalization might occur during follow-up, usually within the first 4 weeks. The pathophysiology of peri-procedural RAO is related to the association of slow or no flow due to vessel compression with vessel injury which leads to acute thrombosis which ultimately create partial or total vessel occlusion.

There is therefore a need for a system that would reduce significantly reduce the risks of RAO.

SUMMARY

A medical device and method to apply an adjustable pressure on a plurality of different vessels, which could be for example an artery and a vein, or more generally two or more arteries or vessels. The device can be used to apply independent but simultaneous pressures on instrumented and non-instrumented vessels. By applying pressure in an individual and distinct manner on each one of the vessels, the primary goal is to reduce flow in one vessel and augment flow in the other vessel. Different mechanisms such as ratcheting, mechanical interlocking or bi-stable locking systems for example, may allow to precisely fine-tune the pressure to different degrees in distinct and separate vessels. One potential application would be to prevent vessel bleeding and blood loss if one vessel has been damaged or punctured and compression on the other vessel may allow to maintain tissue perfusion until hemostasis is completed. This can be particularly useful if vessels are connected proximally (i.e., presence of a nearby bifurcation).

According to an embodiment, there is provided a device for applying an adjustable and simultaneous compression on vessel access points, the device comprising:
  a frame comprising a body with at least two cavities through the body to be placed about surfaces of a patient corresponding to the at least two cavities;
  at least two compression members to be movably fitted in the corresponding at least two cavities, wherein a portion of the frame defines a space into which a portion of the compression member is fitted and around which it hinges, a side of each one of the at least two compression members opposite a portion around which it hinges comprising a locking mechanism which engages with the frame at an interface between said side and the frame to lock each one of the at least two compression members in a given hinge position for applying the adjustable and simultaneous compression by each one of the at least two compression members.

According to an embodiment, the locking mechanism comprises ratchet teeth which are asymmetrical to allow downward movement only.

According to an embodiment, the side of each one of the at least two compression members comprising the teeth is curved with a constant radius of curvature therealong.

According to an embodiment, each of the at least two compression members comprising a bottom surface having a constant radius of curvature along a bottom thereof to provide patient comfort during wearing.

According to an embodiment, the at least two compression members are made of a rigid material.

According to an embodiment, there is further provided a pad along a bottom surface of each one of the at least two compression members.

According to an embodiment, the pad comprises a hole forming a window for viewing through the pad.

According to an embodiment, the pad comprises a transparent portion forming a window for viewing through the pad.

According to an embodiment, each of the at least two compression members is made of a transparent material for viewing therethrough.

According to an embodiment, the at least two compression members comprise exactly two compression members.

According to another aspect, there is provided a device for applying an adjustable compression on a vessel access point, the device comprising:
 a frame comprising a body forming a cavity to be placed on a vessel access point;
 a compression member to be movably fitted in the cavity, wherein a portion of the frame defines a space into which a portion of the compression member is fitted and around which it hinges, a side of the compression member opposite a portion around which it hinges comprising teeth which engage with the frame at an interface between the teeth and the frame to lock the compression member in a given hinge position for applying the adjustable compression onto the vessel access point depending on the hinge position.

According to an embodiment, the teeth are ratchet teeth which are asymmetrical to allow downward movement only.

According to an embodiment, the side of each one of the at least two compression members comprising the teeth is curved with a constant radius of curvature therealong.

According to an embodiment, each of the at least two compression members comprising a bottom surface having a constant radius of curvature along a bottom thereof to provide patient comfort during wearing.

According to an embodiment, the at least two compression members are made of a rigid material.

According to an embodiment, there is further provided a pad along a bottom surface of each one of the at least two compression members.

According to an embodiment, the pad comprises a hole forming a window for viewing through the pad.

According to an embodiment, the pad comprises a transparent portion forming a window for viewing through the pad.

According to an embodiment, the pad comprises an absorbent material which is impregnated by a pharmaceutically active substance.

According to an embodiment, each of the at least two compression members is made of a transparent material for viewing therethrough.

According to an embodiment, at the interface between the teeth and the frame, the frame comprises a portion which can be retracted for disengaging the teeth to hingeably move the compression member freely.

According to an embodiment, the frame has a bottom surface being curved along a width of the frame, and not curved along a length thereof, to provide a shape of a portion of a cylinder to adapt to a shape of a body member.

According to an embodiment, there is further provided a band forming a bracelet, wherein the frame is secured to the band.

According to an embodiment, the band comprises an opening and the frame is insertable into the opening for securing the frame to the band, and releasable from the opening for detachment of the frame from the band.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

Figure 1:
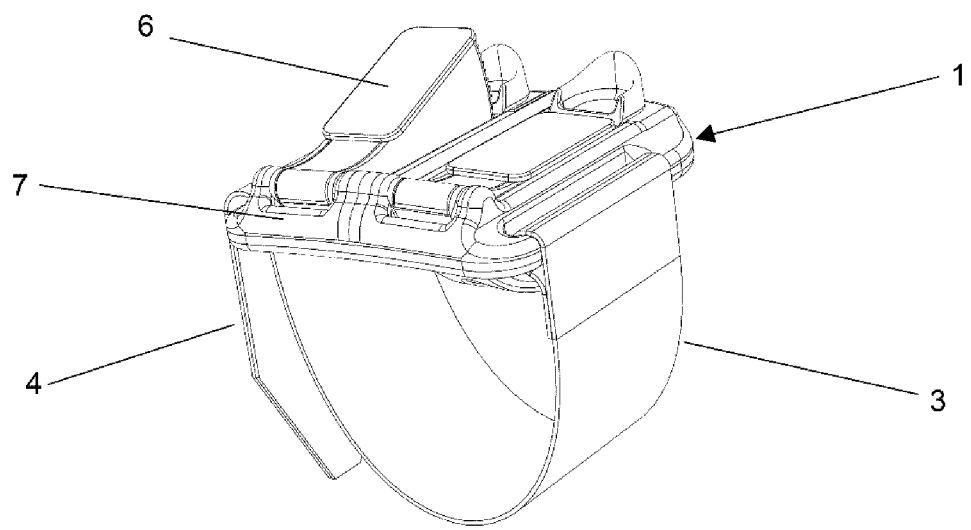
FIG. 1 is a perspective view illustrating a device for applying an adjustable and simultaneous compression on vessel access points, according to an embodiment.

Recent studies have shown that if radial flow can be maintained to some degree during the hemostasis period, the risk of RAO is significantly reduced. That technique has been called "patent-hemostasis". The protocol is rather simple as it involves applying minimal pressure required to obtain hemostasis on the vessel which has been used for access. Once the hemostasis device such as a band, gauge, bracelet or plastic bladder has been applied, the operator will verify that some anterograde flow is maintained either by assessing the flow directly with non-invasive technique such as Doppler or indirectly by measuring oyxmetry-plethysmography on 1 distal finger while pressing firmly on the non-instrumented vessel (i.e., ulnar artery in case of radial access). By creating a distal temporary partial or complete obstruction in the non-instrumented vessel this might produce flow acceleration and increase flow volume in the radial artery (ref), hence maintaining radial artery flow until hemostasis is achieved, usually in less than 5 hours (more frequently 1-2 hours).

Interestingly, it has also been shown that compressing the non-instrumented artery for about 60 minutes, could help recanalization of occluded instrumented vessel. So, compressing the ulnar artery for 1 hour might serve as a non-pharmacological method to safely re-open occluded radial artery after diagnostic angiography and/or intervention.

Mean rate of RAO post-catheterization is usually in the range of 5% without dedicated protocols to preserve anterograde flow during hemostasis. Using "patent-hemostasis" protocol without homo-lateral compression of non-instrumented artery will reduce the risks of RAO to 2-5% at 30 days after per-cutaneous procedure and RAO might even been reduced below 2% if a patent-hemostasis protocol is complemented by ulnar artery compression or occlusion until hemostasis is achieved.

Avoiding peri-procedural RAO is not only important to avoid any potential distal hand ischemia but it is also very important to preserve radial artery patency to allow repeat access in case of additional per-cutaneous procedure or the potential use of a radial artery segment in case of coronary artery bypass graft surgery (CABG). Maintaining radial artery patency could also be important if patient has chronic kidney failure and arterio-venous fistula could be required to permit hemodialysis.

In intensive care units, arteries at the wrist level (radial or ulnar) can also be used to monitor arterial pressure in critically ill patients or during operations. In those cases, anesthesiologists or intensive care physicians will place intra-arterial canula which may remain in place for several hours in case of operation or for several days in critical patients. In most cases, no anticoagulation is given to patients and no specific method or dedicated device is used upon cannula removal to avoid RAO. Manual compression is usually applied until bleeding stops and a simple bandage is left in place for a few hours to prevent re-bleeding. Rates up to 20% of radial artery occlusion have been reported after prolonged cannulation of radial artery in intensive care units.

Although there are simple hemostasis devices to compress an instrumented vessel or after sheath and catheter (e.g., as described in U.S. Pat. No. 8,556,928), there is no device which allows adjustable pressure of two or more vessels simultaneously. Pancholy et al. (U.S. Pat. Nos. 9,510,838 and 9,642,628) have proposed to use a bracelet-type using 2 plastic bladders which can be inflated using air and syringe but we have found that this device does not perform safe and effective dual artery compression. Pressure applied by the plastic bladders is not directly applied on the arteries, and as a result, it may provide significant discomfort to patients. Most importantly, it does not allow to adjust independently different pressures on instrumented and non-instrumented vessels with precision. Lastly, the use of air to inflate the bladders might be associated with significant leakage hence the pressure to be maintained on the instrumented artery during hemostasis and the pressure on the non-instrumented artery might change over time and hence, arterial flows might be affected in both instrumented and non-instrumented vessels. Furthermore, air is compressible. Therefore, the pressure applied by the inflated air-filled bladders may vary over time, hence thereby pressure can be insufficient to prevent bleeding or ineffective to raise pressure flow in the instrumented vessel.

The device according to the invention should address such drawbacks.

Now referring to FIGS. 1-13, according to an embodiment, the device 1 exerts physical pressure onto a surface of the skin, directly on top of the catheter insertion access site in order to achieve hemostasis and thus promote tissue healing of the access site. The pressure is applied after removing the catheter from the patient.

Figure 2:
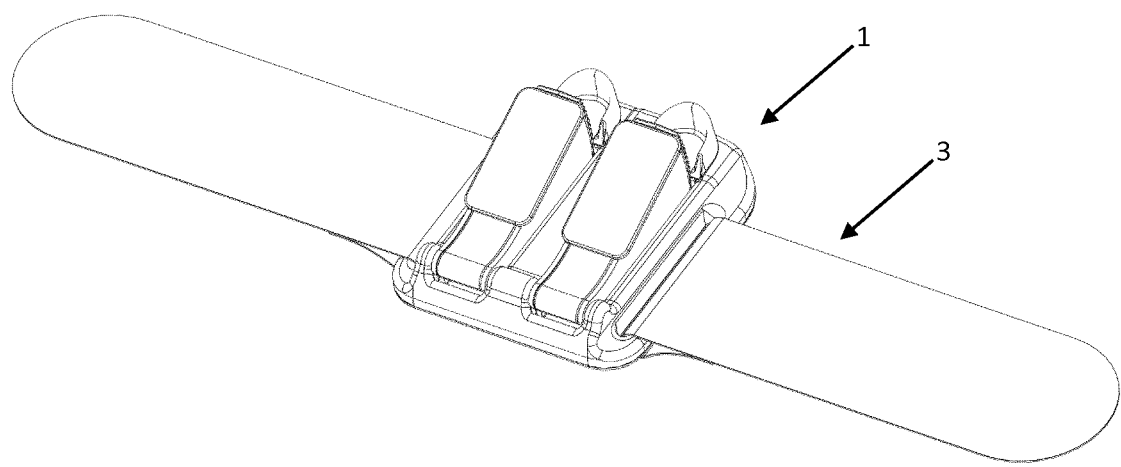
FIG. 2 is a perspective view illustrating the device with the wristband open, according to an embodiment.

Although most examples given herein relate to the wrist, the device is intended to be used on the patient's wrist, leg, arm, forearm, chest, back, thigh or any other body part. The device as shown in FIGS. 1-2 can be attached to the body by means of assembling its main components to a self-locking bracelet with bands 3 or straps 4. It can also be attached to the body by assembling its main components to adhesive pads that are to be attached to the body.

An example of use of this hemostasis device is to use it as a wound closure device after a cardiovascular catheterization where puncture of an artery occurs. However, it can be used for any type of puncture where there is a need to stop bleeding and promote healing.

Figure 3:
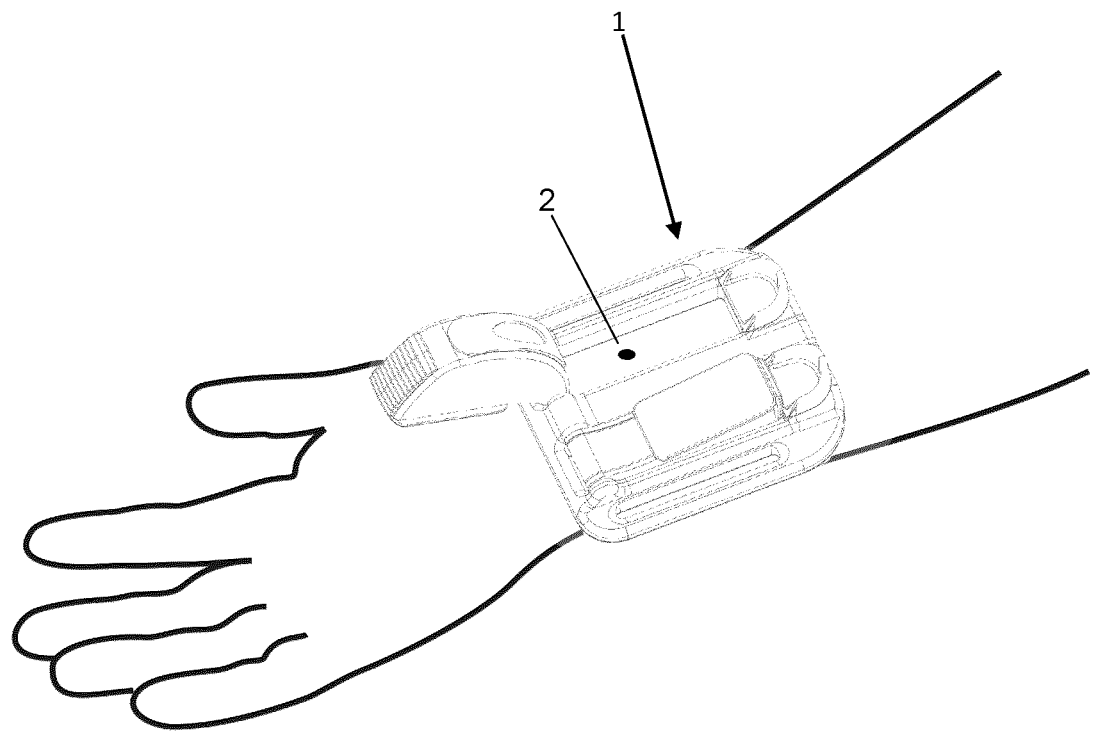
FIG. 3 is a perspective view illustrating a device for applying an adjustable and simultaneous compression on vessel access points, installed on the wrist with one compression member being engaged and the other being disengaged and opened, showing the puncture site, according to an embodiment.

A more specific example of the use of this device is to compress against the skin of the patient on top of the puncture site 2 above the radial artery at the wrist area after radial access catheterization (as shown more specifically in FIG. 3). A hingeable compression member component 6, or preferably more than one hingeable compression member component (i.e., two or even more) can be used on one or multiple sites to promote hemostasis of the radial artery.

However, a condition called Radial Artery Occlusion (RAO) may derive from the prolonged used of a single compression component against one artery, which renders such artery with a permanent collapse and thus unable to use anymore or cause potential tissue ischemia in the hand area. This collapse may be caused by the artery's inability to sustain the compressive force due to insufficient internal pressure.

To prevent and reduce the RAO clinical condition, we have found that using more than one, i.e., at least two compression members onto the skin surface at the puncture site, can be useful. The device 1 according to a preferred embodiment therefore comprises a plurality of hingeable compression members 6, which may be used simultaneously onto different but adjacent locations to distribute flow and pressure among the multiple arteries in the arm. For example. by compressing the ulnar artery with a second compression member in addition to a first compression member, flow and pressure both increase in the radial artery, thereby preventing collapse and thus reducing the risk of RAO. This effect, which the proposed device promotes efficiently thanks to its at least two compression members and to the way they apply pressure, is called patent hemostasis.

The physical pressure can be applied in a distinct and differentiated manner to each one of a plurality of vessels in order to improve the efficacy of the healing process. The device 1 for hemostasis exerts a compressive force on top of the puncture site 2 after a percutaneous intervention. The device is intended to be use by a clinician or a healthcare provider to stop the bleeding and promote the healing of the access wound by exerting oppressing forces on top of the skin by a compression member.

As described in greater detail further below, according to an embodiment, a ratchet-type mechanism is used, after pushing down a wedge component around its pivot rotation point to provide compression, to lock that component in place to maintain the desired constant level of pressure onto the skin surface at the corresponding location.

Figure 9:
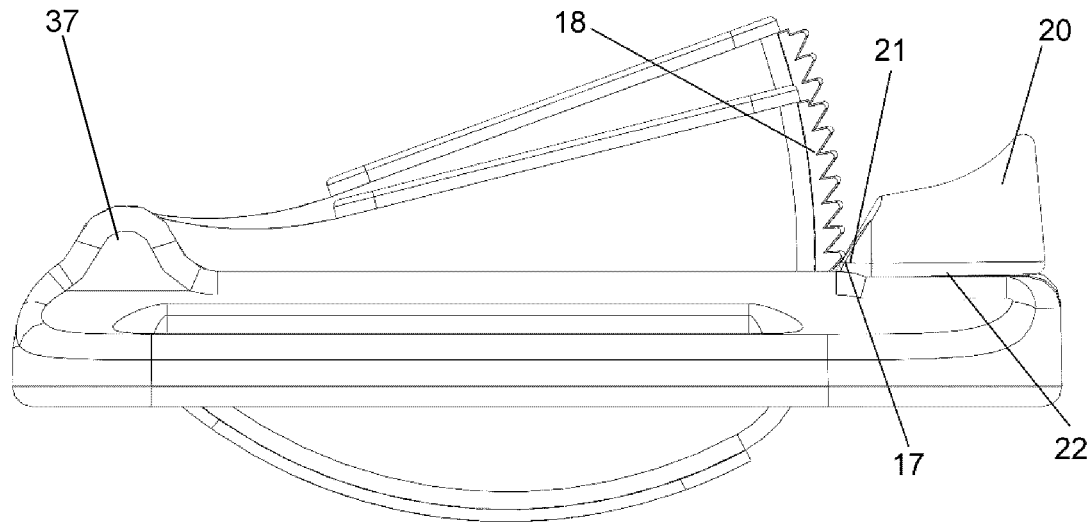
FIG. 9 is a side view illustrating a device for applying an adjustable and simultaneous compression on vessel access points, with the compression members being both engaged, but at slightly different angles and therefore different pressures, according to an embodiment.

There is described a device which applies pressure on a plurality of vessels at the same time, i.e., simultaneously on two different nearby locations on the skin, where typically at least one of the locations is the access point for an instrument on the wrist. The device allows the pressure to be applied independently on each vessel, such that the distinct and independent pressure can be set, for each location on the skin, to a different level and independently from each other, as well shown for example in FIG. 3 or 5. FIG. 9 further shows very well that each compression member 6, from the at least two in the device 1, can be engaged and locked (by the ratchet teeth 15) in slightly different positions (taking into account that each compression member 6 is independent from the other as they are distinct and separate and so is the mechanism for engaging and locking them in a given angle), making sure that each of them applies its own, independent pressure which derives from the angle in which it is locked. The angle and therefore the pressure can be changed since the compression members 6 are movably fitted (i.e., they can hinge and thereby perform a vertical displacement) into the cavities 8.

In the preferred example of obtaining hemostasis on the radial artery access site after catheterization, a moderate pressure can be applied by ratcheting or interlocking mechanisms where the nurse or the physician applies pressure until bleeding stops, then the operator can maintain the pressure with the locking system of the device (namely the locking system of a first one of the compression members 6).

Using the second one of the compression members 6 of the device, the operator can then also apply pressure on the non-instrumented artery (i.e., the other nearby location on the skin). Once the desired pressure is obtained, a separate (second) locking mechanism, distinct from the first one (i.e., as it is the locking mechanism of a second one, or the other one, of the compression members 6), can be engaged (or actuated) to maintain pressure. Hence, until the locking mechanisms on both arteries are disengaged from the teeth, the pressure as determined by the operator is maintained without changes by any engaged one of the locking mechanisms. These locking mechanisms also prevent the patient to manipulate them and inadvertently release the ratcheting mechanisms which could lead to immediate bleeding if pressure is not applied on the access-site and hemostasis is not completed yet.

This mechanism allows to apply simultaneous yet different levels of pressure on instrumented and non-instrumented vessels. Using either direct assessment by doppler or indirect assessment by oximetry-plethysmography or thermography of radial artery flow, the operator can decide to increase or to decrease pressure with the device on both arteries in order to maximize radial artery flow and reduce ulnar artery flow, while maintaining patient comfort and adequate hand perfusion until hemostasis is completed. In this preferred embodiment, the device is primarily used to prevent radial artery occlusion after transradial catheterization. In the event that the ulnar artery was the instrumented vessel, the operation can be simply reversed. In that case, the operator will determine separate pressures on radial and ulnar arteries using the ratcheting mechanisms and the locking systems on both sides but it is anticipated that higher pressure will be applied on the radial artery to increase blood flow in the ulnar artery until hemostasis is achieved. These two examples illustrate how the device can be used in order to prevent artery occlusion during and after hemostasis.

In the event that radial artery occlusion is diagnosed early after sheath or cannula removal, the device can also be applied as a therapeutic device. In that case, the operator might apply maximal (occlusive or semi-occlusive) pressure on the non-instrumented artery in order to increase pressure perfusion in the instrumented vessel. The operator might choose to apply maximal pressure (range from a force 200 grams to up to 5 kilograms to an area round 1-2 $cm^2$) or determine pressure using direct or indirect methods to assess blood flow in the instrumented and non- instrumented vessels.

In order to apply separate and controlled pressures with a high degree of precision and stability on the instrumented and non-instrumented vessels, the device can build upon those separate mechanisms.

Figure 4:
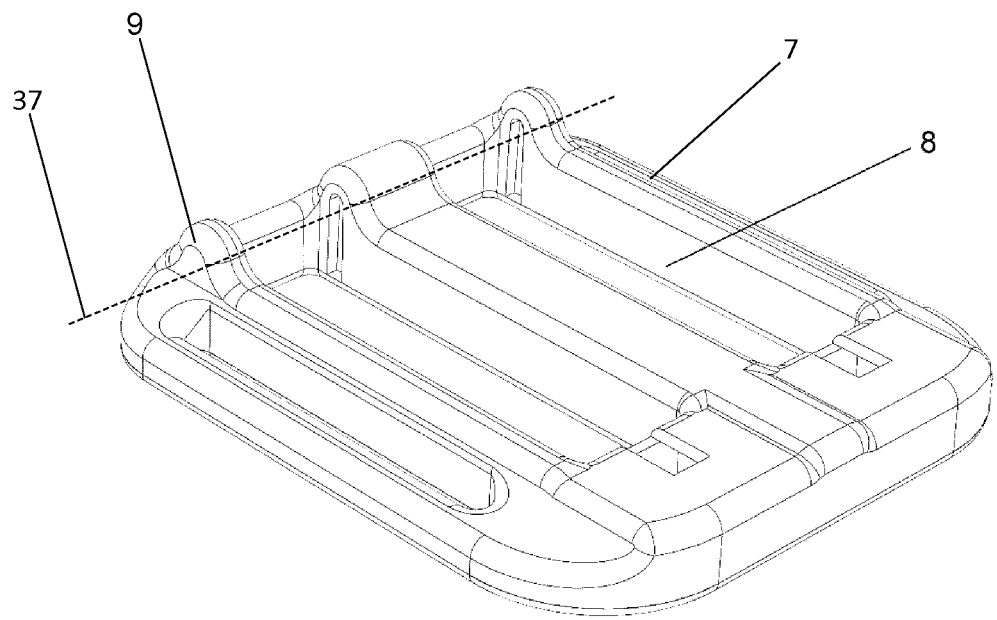
FIG. 4 is a perspective view illustrating a frame of a device for applying an adjustable and simultaneous compression on vessel access points, according to an embodiment.

A main support structure, or frame 7 to which the other components of the device are secured. The frame 7 may be made of a rigid metallic material such as stainless steel, aluminum alloys, titanium alloys or polymeric materials such as ABS, polycarbonate, polystyrene, polysulfone, PVC, nylon or any other biocompatible polymeric material. The main support structure 7 may also be made of flexible materials such as closed cell or open cell foams or elastomeric rubbers. The main support structure or frame 7 serves as the main frame to which the other components are secured. The frame 7 has a solid body defining a periphery and intermediate portions, wherein the external shape of the frame 7 may have a rectangular, round or any other polygonal shape, regular or irregular. The main support structure or frame 7 may have one or more rectangular or polygonal cavities 8 (where the portions in between are the so-called intermediate portions belonging to the body) or hollow shapes to allow the placement of one or more compression members 6 in the specifically defined distinct areas in the cavities 8, as shown in FIG. 4. The cavities are through the frame (from top to bottom) to be accessible on the top, and to reach the patient skin surface on the bottom.

Figure 5:
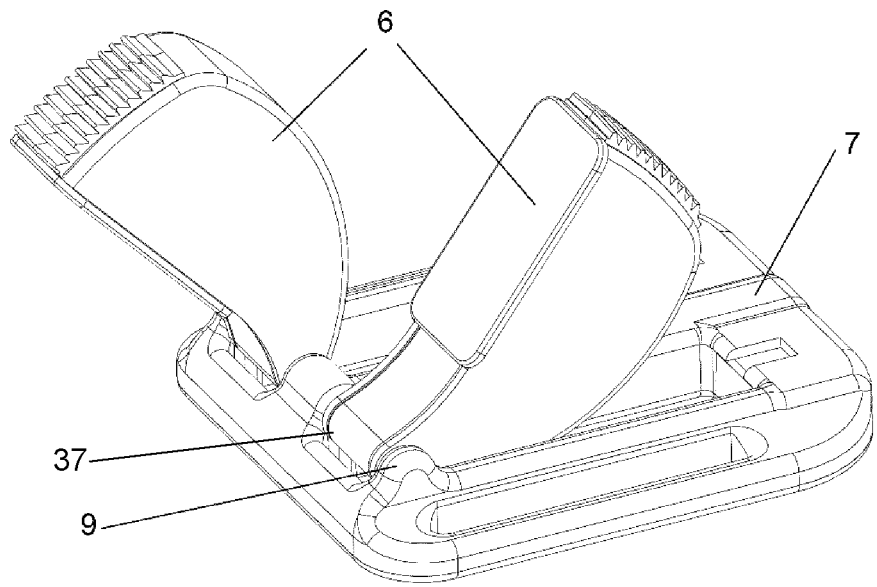
FIG. 5 is a perspective view illustrating a device for applying an adjustable and simultaneous compression on vessel access points, with the compression members being disengaged and freely hinged at different angles, according to an embodiment.

According to an embodiment. the device 1 comprises one or more compression members 6 that are assembled to the frame 7 through a hinge mechanism 9. The hinge mechanism 9 of the frame 7 comprises a portion of the body of the frame 7 having apertures along a hinge axis 37, as shown in FIG. 4, and the compression members 6 have their hinge mechanism 9 at that location, as shown in FIG. 5, making the compression members 6 hingeable, i.e., they can hinge about that hinge axis 37 (i.e., they can rotate about that pivot). A pin, rod or any other element may embody the hinge axis 37, or otherwise, the side portions of the compression members 6 may be slightly larger at that point such that they can be clipped in a snap-fit relationship with the hinge mechanism 9 of the body of the frame 7. The hinge mechanism 9 is the portion of the frame 7 which defines a space into which the compression member 6 will be fitted and around which it will hinge subsequently.

Figure 6:
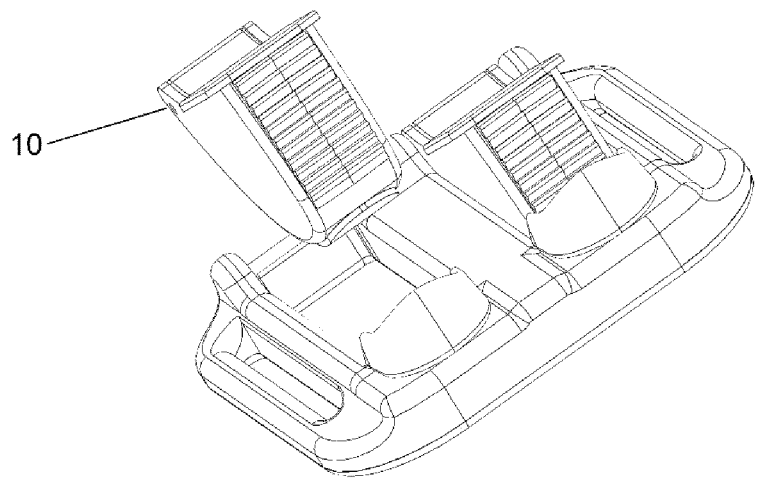
FIG. 6 is a perspective view illustrating a device for applying an adjustable and simultaneous compression on vessel access points, with one of the compression members being dismounted from the frame, according to an embodiment.
Figure 7:
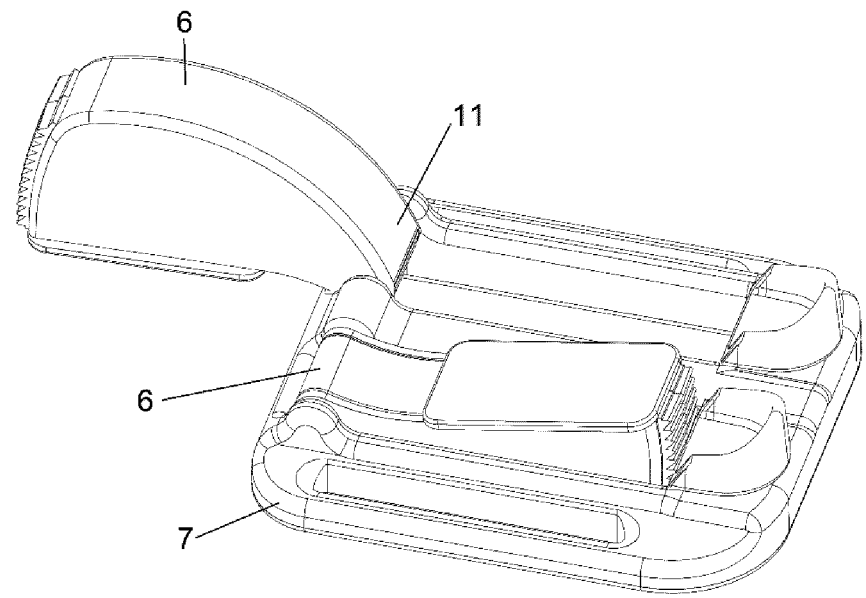
FIG. 7 is a perspective view illustrating a device for applying an adjustable and simultaneous compression on vessel access points, with one of the compression members being widely hinged at a maximum angle, according to an embodiment.

The compression members 6 rotate freely around the hinge pivot point 9 which can be located at any point in the frame 7. The movement of these components causes them to compress against the skin of the patient. The compression members 6 can be attached permanently or be dismountable (configuration 10, as shown in FIG. 6) from the support structure for re-utilizing them. The mechanism can turn 180 degrees or more (configuration 11, as shown in FIG. 7) to expose the skin surface to verify that hemostasis has been achieved without removing the rest of the device.

Depending on the embodiment, the compression members 6 can be made of a rigid polymer (or other rigid material), or of a flexible polymer (or other flexible material), and can be opaque or transparent. In the embodiment where the compression members 6 are transparent, such transparency will allow for the proper and accurate positioning of the device on top of the puncture site 22 after cardiac catheterization. In other words, the puncture site 2, as shown in FIG. 3, can be seen from outside even in the case where the compression members 6 would be engaged.

Figure 8:
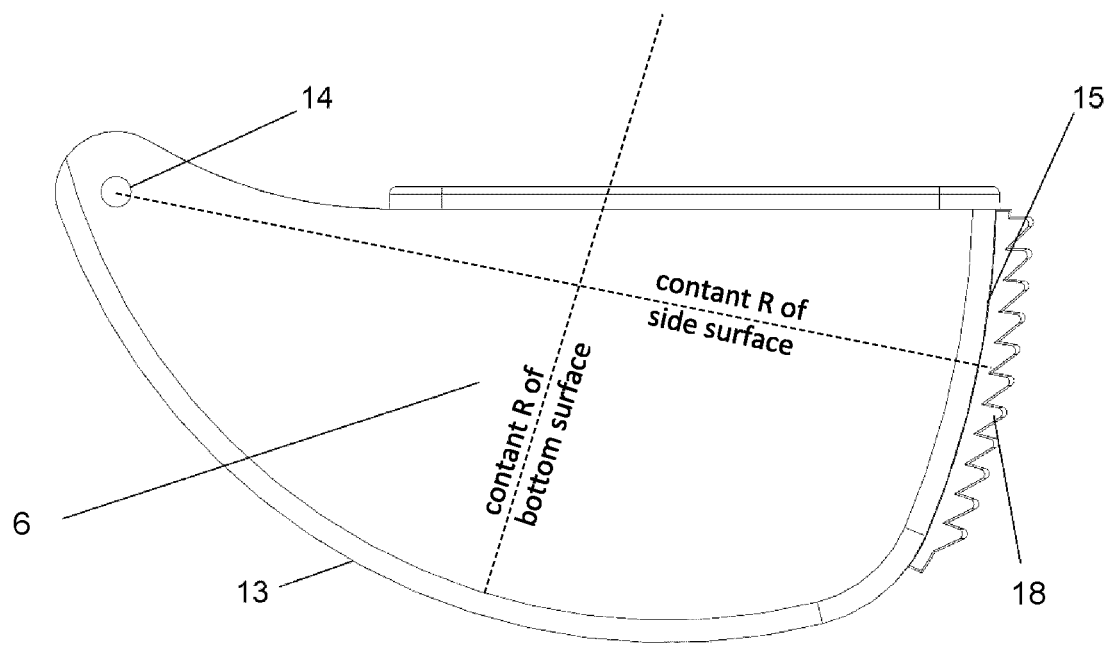
FIG. 8 is a side view illustrating one of the compression members, including the different radiuses of curvature, locally constant over specific ranges (bottom, side), according to an embodiment.

The bottom geometry of the compression member 6 is the compression member bottom surface 13, which has a constant radius of curvature that enables its movement to compress the body surface including the puncture site 2 with a constant geometrical pattern and thus maximizes patient comfort as no sudden changes of geometry or sharp areas are present. FIG. 8 shows well that the compression member bottom surface 13 is curved, and it can be seen that this region of the compression member 6 has a constant radius of curvature. The radius of curvature changes on the sides of the compression member 6, but remains substantially constant on the bottom thereof, corresponding to the bottom surface 13. The bottom surface 13, characterized by that constant radius of curvature, should be long enough to cover the puncture site 2 and around the puncture site 2. Other parts of the compression member 6 do not need to have the same radius of curvature, e.g., close to the hinge point 14. The side surface also has the ratchet teeth 15 with its own constant radius of curvature. Therefore, there are different radiuses of curvature, locally constant over specific ranges (bottom, side). Preferably, if the radius of curvature changes between these specific regions of the compression member, the change should be smooth (e.g., the radius of curvature should change regularly, without discontinuity) to avoid any asperity which could cause patient discomfort.

According to an embodiment, the compression members 6 have, at the opposing end of the hinge point 14, a locking mechanism. According to an embodiment, the locking mechanism is a ratchet-type locking mechanism comprising ratchet teeth 15. According to another embodiment, it is a gear-teeth type locking mechanism comprising a worm gear 16 (shown in FIG. 10 and discussed briefly further below in relation with alternative embodiments).

The side surface of the compression member 6 which comprises the ratchet teeth 15 is curved, with the hinge point 9 defining the center of the radius of curvature of that side surface. This curved geometry enables the ratchet teeth 15 to engage in the locking mechanism with a constant force as the tooth engagement occurs at the same distance without any mechanical deformations of the compression member, thus the same level of force is exerted by the spring-loaded engaging mechanism 17 at any given position or angle. This same level of locking force enables the healthcare practitioner to feel the same level of force when releasing the locking mechanism through the action of the release sliding button throughout the entire teeth track.

The radius of curvature of the compression member bottom surface 13 at the bottom of the compression member 6 is between 30 and 100 mm and of constant radius in order to maximize patient comfort. A constant radius of curvature is needed to maintain the same geometry against the patient's skin at any given position of the compression member. The larger radii would provide maximized comfort for the patient as the compressive forces will be more evenly distributed.

The compressive forces applied to the skin are caused by the motion of the compression members and by the retainment of the compression member 6 in place afterwards. The healthcare practitioner pushes the compression member and it travels and engages with the ratchet teeth allowing for a one-way directional travel at the interface 18, on the side surface of the compression member 6. A plurality of compression members 6 can be used to exert compressive forces on multiple areas of the skin and each compression member works independent from each other. Thus, each compression member can exert its own desired level of force on the skin surface.

The one-way directional travel is obtained by having the ratchet teeth asymmetrical. Each tooth of the ratchet teeth 15 has a triangular shape comprising two surface extending from the side surface of the compression member, as shown in FIG. 8. The center of rotation of the compression member 6 is the hinge point 14, defining the center for the radius of curvature of the side surface of the compression member 6. For each tooth, a first side of the tooth (top side) is straight, in direction of the hinge point 14, while the other side of the tooth (bottom side) is inclined with respect the radius axis R (shown in FIG. 8). This asymmetry provides the capacity for one-way travel (downward only), where the upward travel is only possible if the ratchet teeth are disengaged.

The ratchet teeth need to be disengageable in order to be opened or readjusted and reengaged to another locking position. According to an embodiment, and as shown in FIG. 9, the ratchet teeth 15, at its interface 18, can be disengaged by actioning a spring-loaded release button 20 that removes the locking interface by disengaging the ratchet teeth from the locking tooth of the release button 21 (i.e., by creating a distance between them which removes the contact between teeth, thereby achieving disengagement). However, preferably, the action of this mechanism has only a limited travel distance to promote a quick disengage and re-engagement of teeth. There may be additional control mechanisms for the gradual release of the ratchet teeth such as worm-gear mechanisms 16 or screw type of components, described further below.

The compression member 6 may be fully released from the ratchet teeth 15 through the use of a spring-loaded sliding button 20 that disengages the ratchet teeth 15 when actioned. while the frame 7 is still in place in the patient. This feature helps the healthcare practitioner to assess and evaluate if full hemostasis has been achieved without removing the entire device.

The compression member 6 may be made of a rigid material or a flexible material. Urging the compression member 6 onto the skin surface provides the desired pressure. The compression member 6 as illustrated is not inflatable or significantly deformable.

According to a preferred embodiment, a transparent material is used to aid in the visualization of the access site on the skin. The highest compressive forces shall be positioned on top of the access site (i.e., the puncture site 2) on the skin. The compression members transparency allows to visualize the access site and thus helps in the proper positioning of the device.

The material of the compression member, while remaining transparent, may be tinted with any color in such a way that if blood is present at the interface of the skin with the compression member 6, it will appear darkened.

Figure 11:
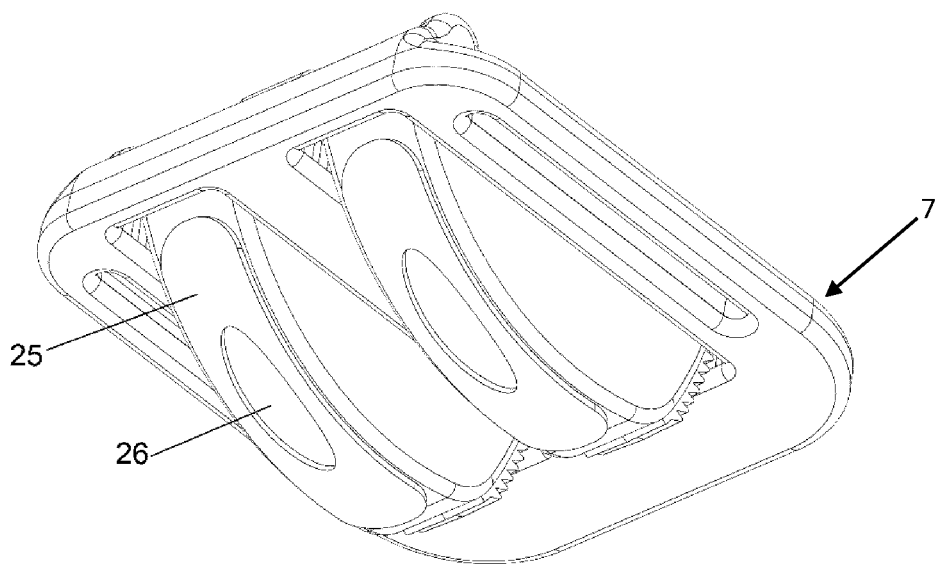
FIG. 11 is a bottom perspective view illustrating a device for applying an adjustable and simultaneous compression on vessel access points, with the compression members being both engaged, and comprising a pad with a window in the pad for viewing, according to an embodiment.

According to an embodiment, and as shown in FIG. 11, the compression members 6 comprise a soft pad 25 made of a suitable padding material (e.g., a material in the form of foam, cushion or fabric) which may be absorbent at the interface 13 between the compression members 6 and the patient skin. This material can be utilized to absorb excess blood coming out of the patient when in use. Preferably, the material may be made of highly absorbent cellulose foam or any other type of biocompatible and sterilizable hygroscopic foam. The soft pad 25 may or may not cover the entirety of the compression member 6 bottom surface 13. The absorbent foam or padding material may have a window 26 of any shape at any particular location of the pad 25 (which can be made of foam) to properly visualize the puncture site 22 from the perspective of the health practitioner (i.e., from above the compression member 6). The soft pad 25 is secured to the compression member bottom surface 13 using any suitable way for attachment (e.g., adhesively attached, sewn, attached with wires, nailed, screwed, soldered, etc.). If present, it can increase patient comfort, reduce allergenicity and enable absorbability in case the patient bleeds while the device is in use. According to an embodiment, the soft pad 25 is absorbent and can be impregnated with a pharmaceutically active substance for application to the patient skin when the device is worn.

According to an embodiment, the compression members 6 may be interchangeable to be replaced for unused ones in the case the main frame remains as a non-disposable component.

According to an embodiment, the motion between the compression member ratchet teeth 15 and the spring-loaded release button 20 produces a clicking sound as each ratchet tooth is advanced during the relative motion between the spring-loaded release button 20 and the ratchet teeth 15, due to the tight engagement at the interface between them and also due to the rigid material which should be used. This sound effect provides an audible feedback as to how much the healthcare practitioner has compressed the device against the skin of the patient. This clicking sound ensures that the healthcare practitioner is notified if the adjusted pressure is being changed. This is true not only during the installation but also during wearing time. For example, using prior art systems involving a balloon with a fluid, the pressure may change over time (e.g., if the temperature of the fluid providing the desired pressure changes over time) and no one is notified of this continuous change over wearing time. With the present device, the ratchet mechanism locking the compression member 6 is a particular position provides a stable position and therefore a stable pressure over time, and if by accident this position changes, a clicking sound is emitted and notifies nearby personnel or the wearer so that a correction can be applied.

Figure 12:
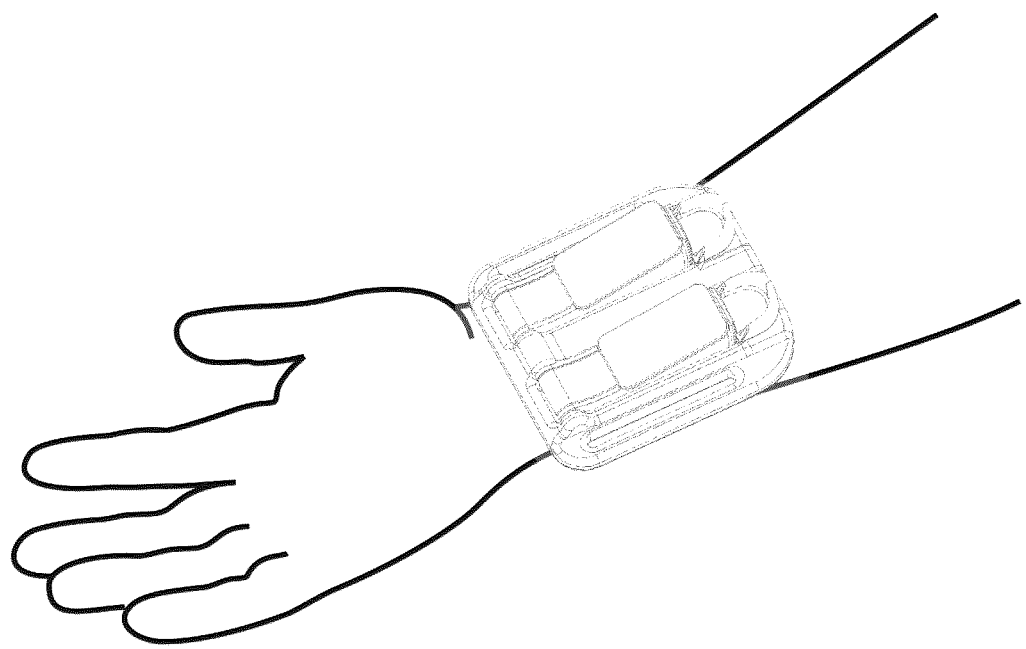
FIG. 12 is a perspective view illustrating a device for applying an adjustable and simultaneous compression on vessel access points, installed on the wrist with both compression members being independently engaged, providing an independent pressure under each one of them onto the skin surface, according to an embodiment.
Figure 13:
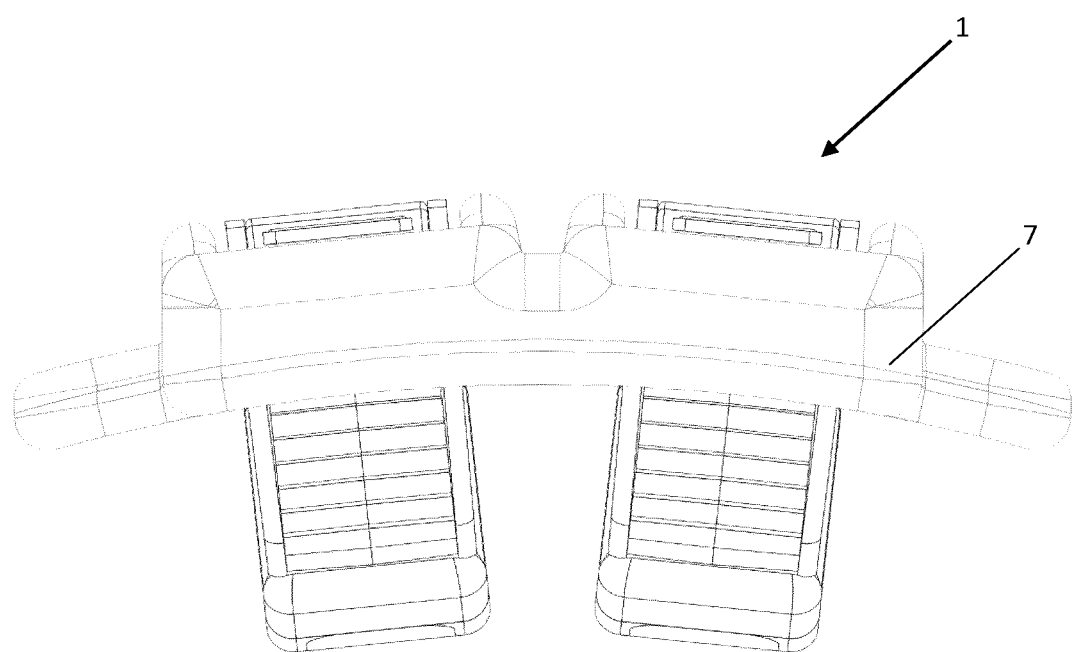
FIG. 13 is a front view illustrating a device for applying an adjustable and simultaneous compression on vessel access points, with both compression members being engaged at the same angle, according to an embodiment.
Figure 14:
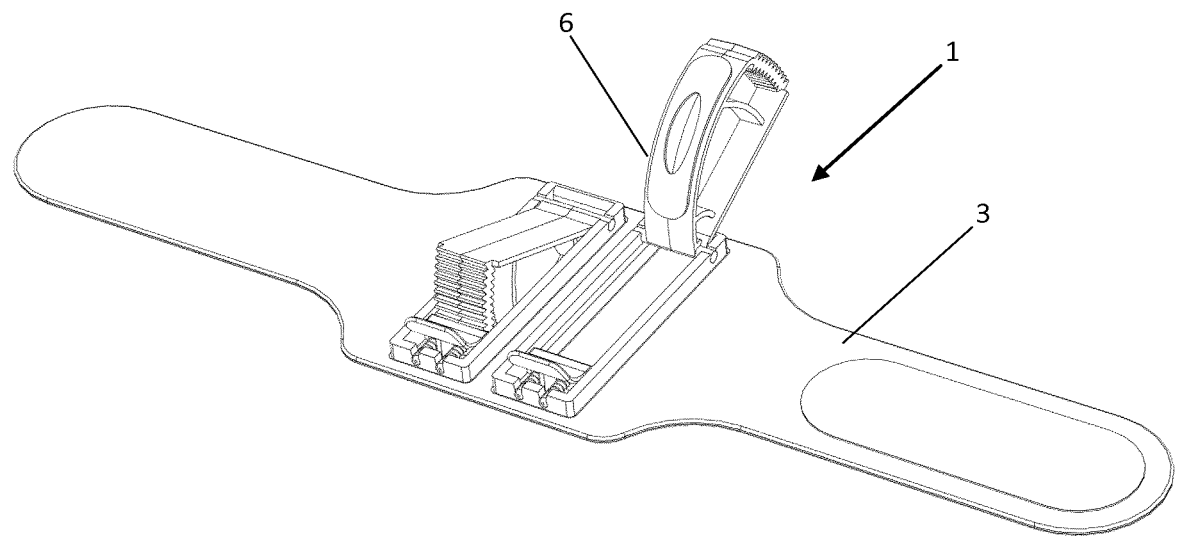
FIGS. 14, 15 and 16 are a front perspective view, a bottom perspective view and a rear perspective view illustrating a device for applying an adjustable and simultaneous compression on vessel access points, with a thin band as a bracelet with the frame inserted in an opening, according to an embodiment.
Figure 15:
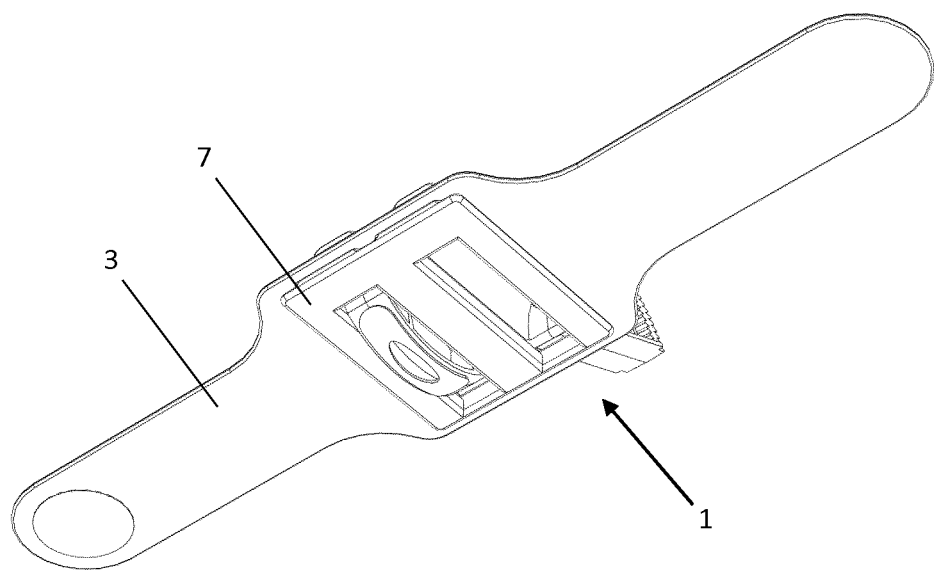
Figure 16:
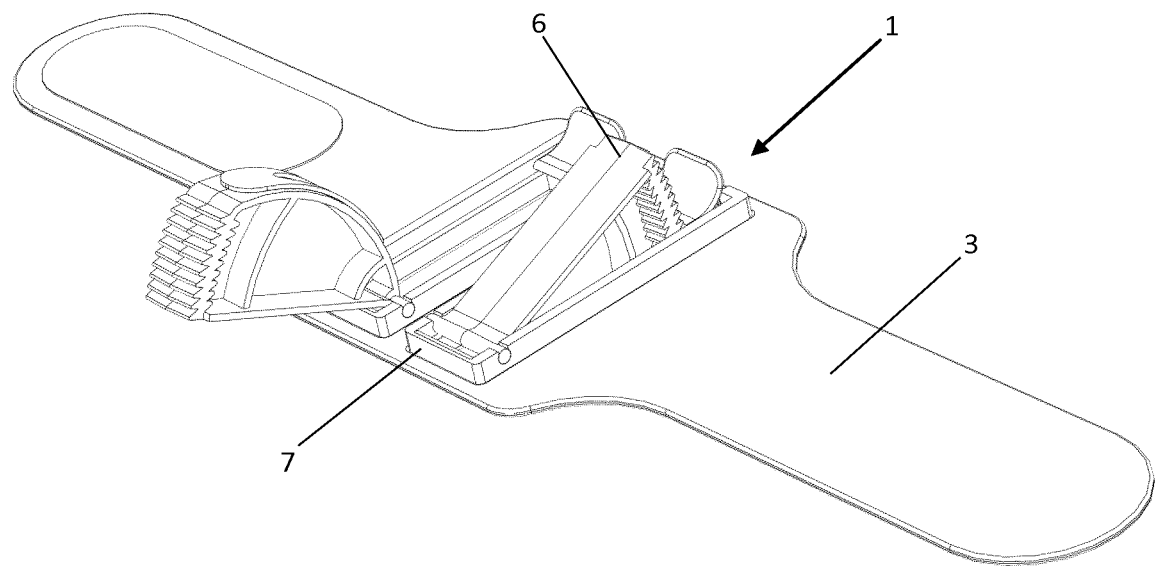
Figure 17:
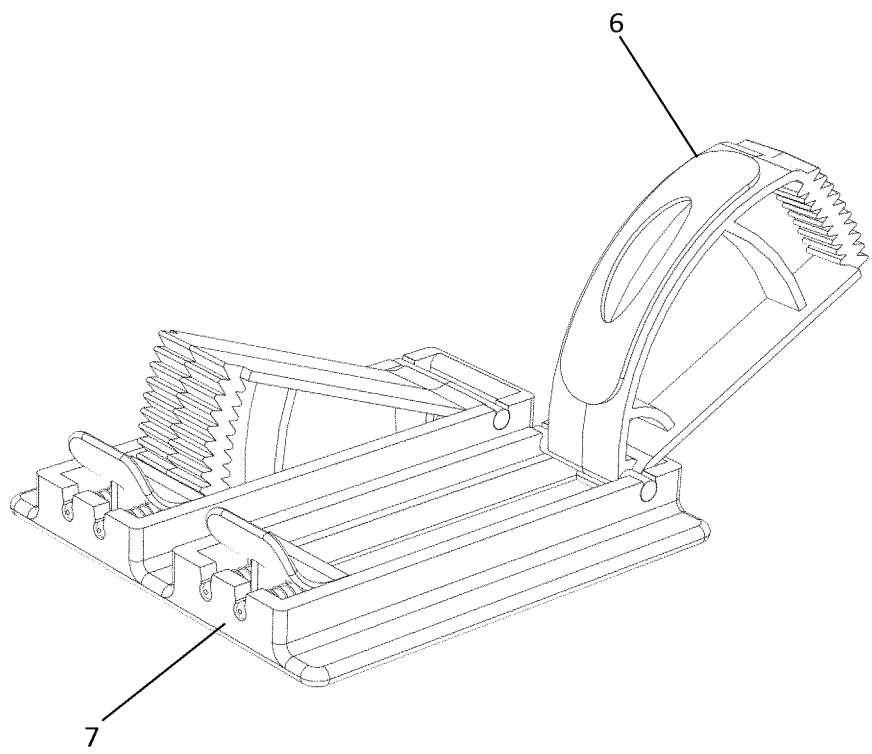
FIG. 17 is a perspective view illustrating the frame of FIG. 14, according to an embodiment.

Due to its symmetrical nature well shown in FIGS. 1-7, and also in FIG. 12 and FIG. 13, the device design is ambidextrous and can be used in any arm and in any orientation with the ratchet teeth facing distally or proximally relative to the patient. Also, as shown in FIG. 13, the frame 7 (and specifically the frame 7, not only the band 3) has an inner surface (or bottom surface) which is curved and concave along the width of the frame 7, but not along the length of the frame 7, which implies that the inner surface of the frame 7 has a shape of a portion of cylinder, thereby being adapted to the shape of an arm or forearm or wrist, or any other suitable body member having a cylinder shape. Accordingly, the top surface of the frame 7, along a width thereof, is curved and convex.

According to an embodiment, the main support structure or frame 7 has open slots of rectangular, round or a plurality of polygonal forms. The open slots have on the internal sides of their walls a hinge mechanism that allows to assemble the compression members at their hinge axis 37. The compression members 6 rotate freely about the hinge or pivot point 37 and are only limited by the interference with the main support structure.

One or more compression members 6 may be present in a device assembly and they may work independently from each other.

According to an embodiment, the device has a flexible band 3, preferably made of self-adhering material or adhesive membranes to be positioned around the wrist or any other anatomical part of the patient where hemostasis is desired. According to an embodiment, the band is wide and should be at least 15 mm in width in order to evenly distribute the pressure in any direction to increase patient comfort. The band is attached directly by looping it around the main structure band slots or by directly attaching the band by adhesive means on top of the main structure.

One advantage of the device is that it uses the lever effect thanks to the hinge axis 37 and the fact that the compression members 6 have their hinge connecting portion or hinge point 14 around that hinge axis 37. When the practitioner presses on the compression member 6, the force can be applied at greater distances away from that pivot point of rotation, and then it becomes easier for the practitioner to press the compression member 6 against the skin of the patient (the force is applied onto the compression member 6 distally from the hinge 14, 37, providing a lever). This effect makes the device easy to use without the need of great forces exerted by the fingers of the healthcare practitioner, assuming that the force is exerted much closer to the part containing the ratchet teeth 15. As the device is being pushed by the healthcare practitioner with the fingers, it provides a natural haptic feedback to the healthcare practitioner on the level of compressive force being exerted by the compression member on the patient, i.e., the more the practitioner needs to force to have the compression member 6 travel down, the greater is the pressure applied on the skin surface at that location.

Other, different mechanisms can be used on the separate parts of the device, according to other embodiments.

Volume displacement: In this alternative embodiment, a rigid structure that contains a non-toxic sterile fluid in a tight-sealed environment can be displaced through a channel inside the structure to inflate a bladder-type membrane and thus apply pressure on the instrumented and non-instrumented vessel access points on the wrist. An adjustable piston allows to determine the level of fluid displacement, and hence the final pressure applied to the vessel.

Ratchet mechanisms: With the ratchet mechanisms as described above, a main structure composed of rigid or semi-rigid material such as plastic, polymer or metal forms an assembly with at least one wedge component with ratcheting mechanisms, with or without interlocking systems. These wedge components can be displaced with two exemplary methods: either with a movement around a pin placed through the main structure or with a linear translational movement. The ratchet teeth allow for a unidirectional or linear translational movement and thus prevent backward displacement from the desired position. As the component moves it creates a pressure on the access-site which can vary.

Figure 10:
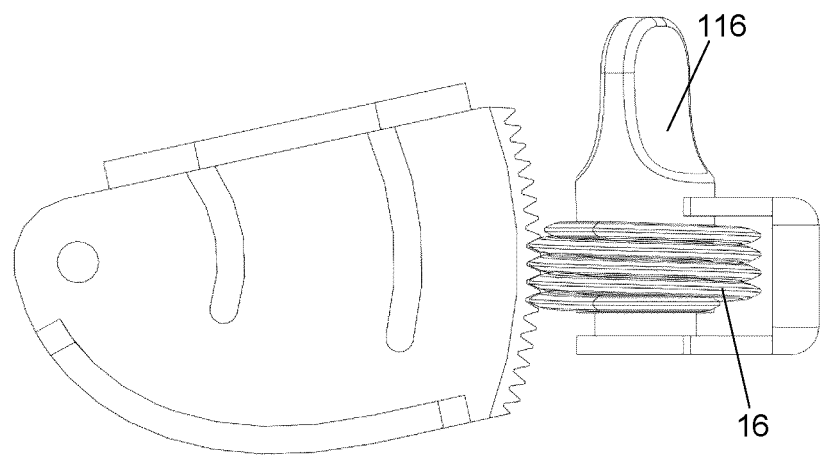
FIG. 10 is a side view illustrating a device for applying an adjustable and simultaneous compression on vessel access points, comprising a worm gear for displacing the teeth, which are in the form of a gear instead of a ratchet, according to an embodiment.

Worm gear mechanisms: With the worm gear mechanism, and as shown in FIG. 10, a main structure composed of rigid or semi-rigid material such as plastic, polymer or metal forms an assembly with at least one wedge component with worm gear teeth 16. A worm shaft 116 is placed next to the gear teeth and the axial movement of the worm shaft creates a displacement of the wedge of toothed wedge and to adjust for fine pressure tuning on the access-site.

Pinion rack mechanisms: With the pinion rack mechanisms, a main structure composed of rigid or semi-rigid material such as plastic, polymer or metal forms an assembly with at least one wedge component with contains a plurality of gear teeth (rack). A pinion gear is placed next to the rack and the movement of the pinion creates a displacement of the wedge to adjust for fine pressure tuning on the access-site.

Interference displacement: With the interference displacement mechanisms, a main structure composed of rigid or semi-rigid material such as plastic, polymer or metal forms an assembly with at least one component with contains a plurality of teeth. The two components are parallel to the main structure (as opposed to the other embodiments which included perpendicular assemblies). The user applies pressure to the components individually to create movements around a pin and the transverse geometry of the wedge creates an interference displacement of the bottom parts of the main structure either by mechanical deformation or by a sliding displacement mechanism.

Screw: With the screw mechanism, a main structure composed of rigid or semi-rigid material such a plastic, polymer or metal holds a plurality of components that have a linear translational displacement through the use of screw-types mechanisms. The actual movement creates a linear translational movement with fine adjustments depending on the pitch of the screw.

Band Adjustment: With the band adjustment mechanism, a main structure composed of rigid or semi-rigid material such a plastic, polymer or metal holds a fixed oppressing structure made of rigid, semi-rigid or flexible silicon rubber. Two ends of a band are inserted through the main structure in a parallel fashion. The two bands have a slotted rack geometry with gear teeth on one of the side of the slot. When the two ends of the band are inserted into the main component in opposite directions, the gear teeth of each of the slotted racks are facing as well in opposite directions. A pinion gear assembled into the main component goes inside the teeth of the slotted racks of the bands. A fine adjusting know is connected to the pinion gear. The movement of the knob creates a movement of the pinion gear which produces a linear translational movement of the bands bringing them closer together or further away depending on the direction of the rotation. This allows to reduce or enlarge the diameter of the looped bands and thus creating downward pressure or relieving it with the fine adjustment of the movement of the knob.

Roller Clamp: With the roller clamp mechanisms, a main structure composed of rigid or semi-rigid material such a plastic, polymer or metal holds a plurality of components which can be in the form of a roller clamp assembly. The roller clamp assembly comprises a flywheel assembled in a linear ratchet slot and the rotation of the flywheel progresses downwards in a diagonal movement as the user rotates the wheel. As the flywheel move downwards, it creates a pressure on top of the access-site.

Bi-stable locking mechanisms: The bi-stable locking mechanism comprises a main structure composed of rigid or semi-rigid materials such as plastic, polymer or metal holds, a plurality of components which can be in the form of a bi-stable locking mechanism. The bi-stable locking mechanism comprises two components which can displaced towards the area of interest in order to induce pressure. The displaced wedge has a nested bi-stable lever that, once sufficient force is applied to such lever, the locking engages maintaining the wedge static relative to the main structure.

Locking mechanisms: The locking mechanism comprises a main structure composed of rigid or semi-rigid materials such as plastic, polymer or metal holds, a plurality of components which can be in the form of a bi-stable locking mechanism. The bi-stable locking mechanism comprises two components which can displaced towards the area of interest in order to induce pressure. Each component comprises a wedge which has a nested knob that, once it rotates a sufficient amount, the locking engages maintaining the wedge static relative to the main structure.

It should be emphasized that similar mechanisms can be used either for both parts of the device or that a combination of different mechanisms can be preferred. The overall objective remains that the user must be allowed to apply separate yet simultaneous pressures as the result of applied forces from 200 grams up to 5 kilograms over 1-2 $cm^2$ of the skin surface to be on the puncture site area on one side and non-instrumented vessel are on the homolateral side.

If desired, the device might contain at the level of the interface surfaces with the skin a coating made of polymers, foams, fabric, silicone-rubber which might improve the comfort of the patient or might as well contain therapeutic pharmacologic compounds such as pro-coagulant agents, antibiotic agents, anesthetic or any organic or non-organic material which could accelerates hemostasis or the healing process to get rapid closure of the puncture site. In a preferred embodiment, the interface surface can be coated or covered with a highly absorbent material such as hydrophilic open-cell foams.

Another embodiment is that the device might contain at the interface surface a thermochromic pigment which is sensitive to temperature and might indicate whether the vessels upon which pressure is applied remain with a substantial blood flow as indicated by colors code based on temperature. Indeed, it has been shown that tissues with adequate perfusion have higher temperature than ischemic or under-perfused tissues.

FIGS. 14-16 and 24-28 show a band 3 forming a bracelet which is made of a flexible material, e.g., an elastomer, and which is thin thereby being flexible. This allows providing the band 3 with any shape and then surrounding the wrist or any other body member with the band 3 by deforming said band 3 and enclosing the body member, taking advantage of the flexible nature of the material and the thinness of the band 3 allowing its deformation.

While FIG. 3 shows that the frame 7 can comprise a slit into which the band 3 is inserted to fix the band 3 (i.e., the bracelet) with the frame 7, both elements can be secured together in a different way. For example, as shown in FIGS. 14-16 and FIGS. 24-28 illustrate that the band 3 can comprise openings 31 into which the frame 7 is fitted and secured.

Figure 18:
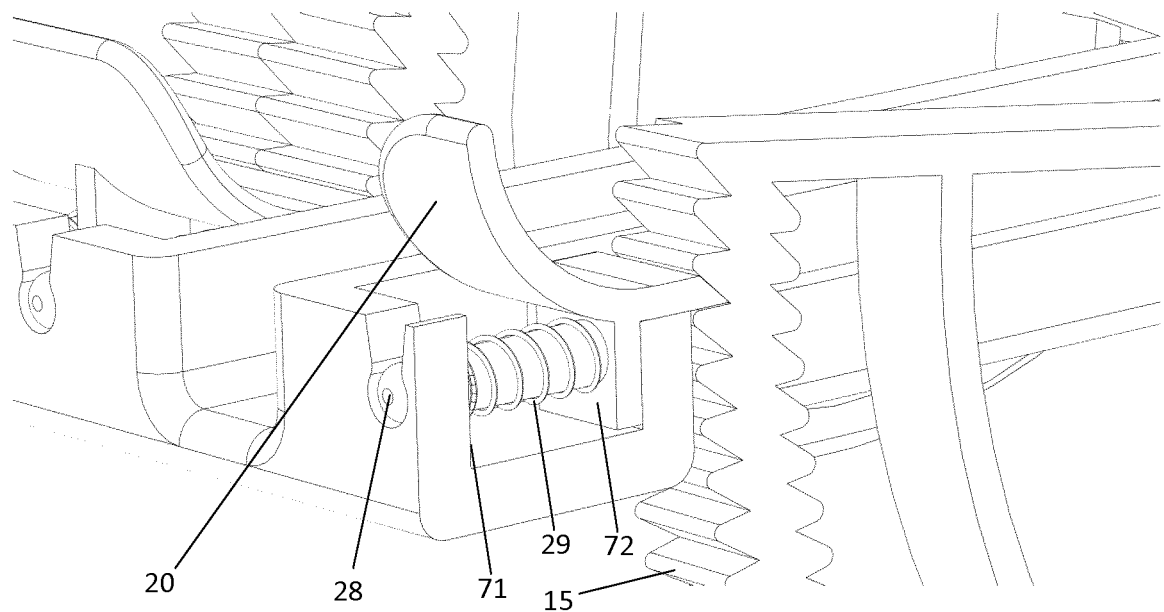
FIGS. 18-19 are close-up perspective views illustrating the spring-loaded sliding button and ratchet teeth on the frame of FIG. 14, respectively in a locked and unlocked positions, according to an embodiment.
Figure 19:
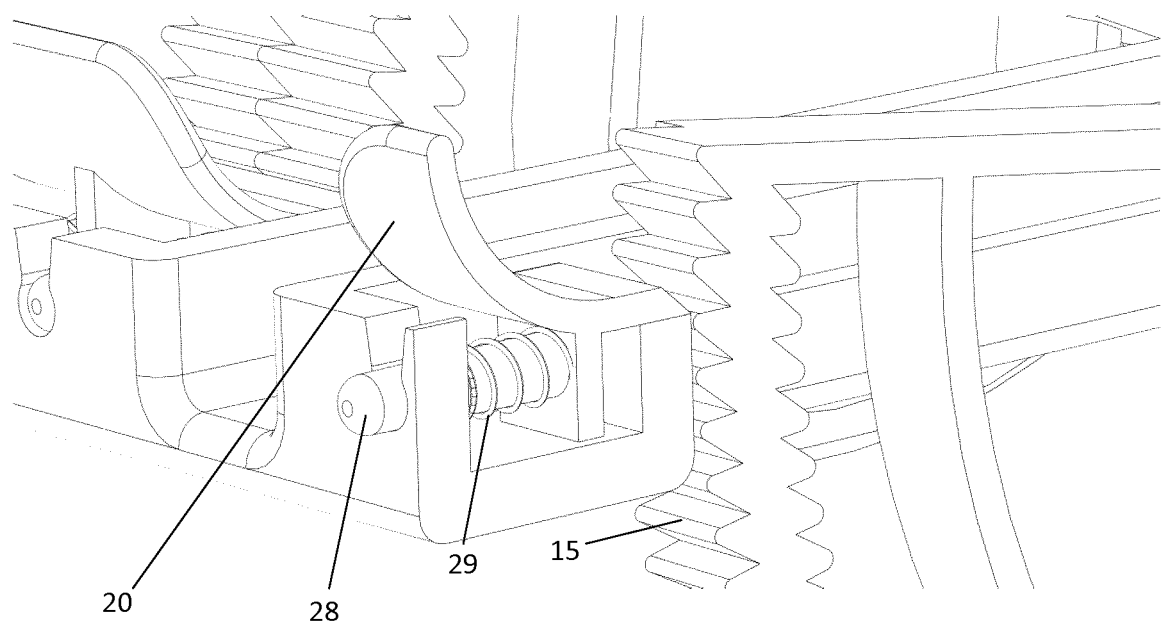
Figure 20:
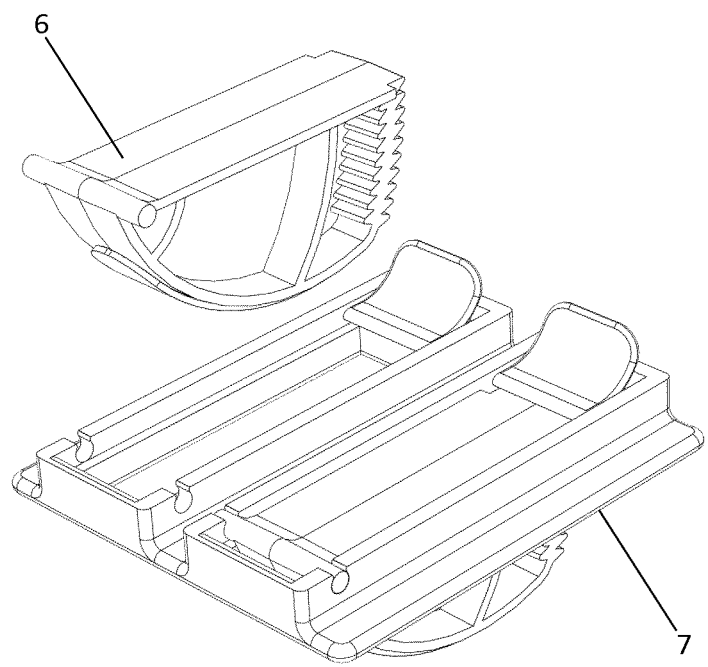
FIG. 20 is a perspective view illustrating the frame of FIG. 17 in an exploded view, according to an embodiment.
Figure 21:
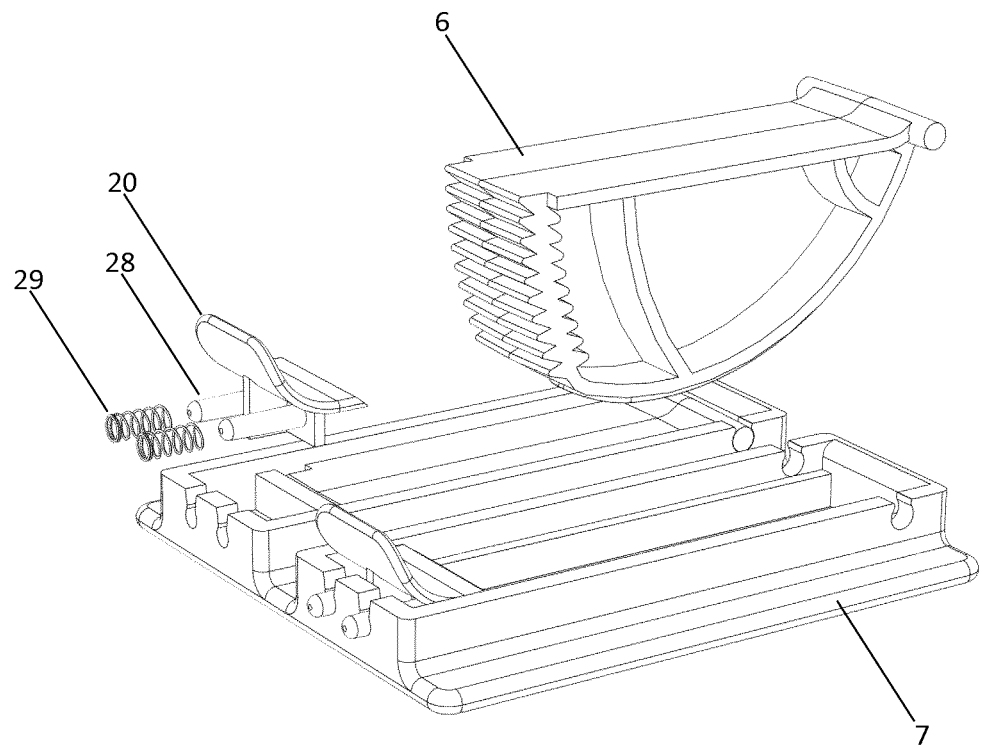
FIG. 21 is a perspective view illustrating the frame of FIG. 17 in another exploded view, according to an embodiment.
Figure 22:
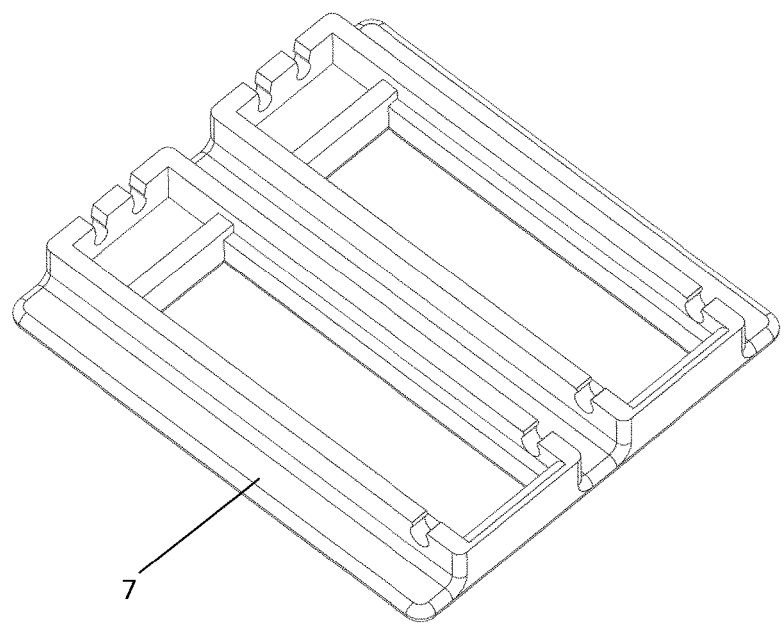
FIG. 22 is a perspective view illustrating the frame of FIG. 17 without any additional component, according to an embodiment.
Figure 23:
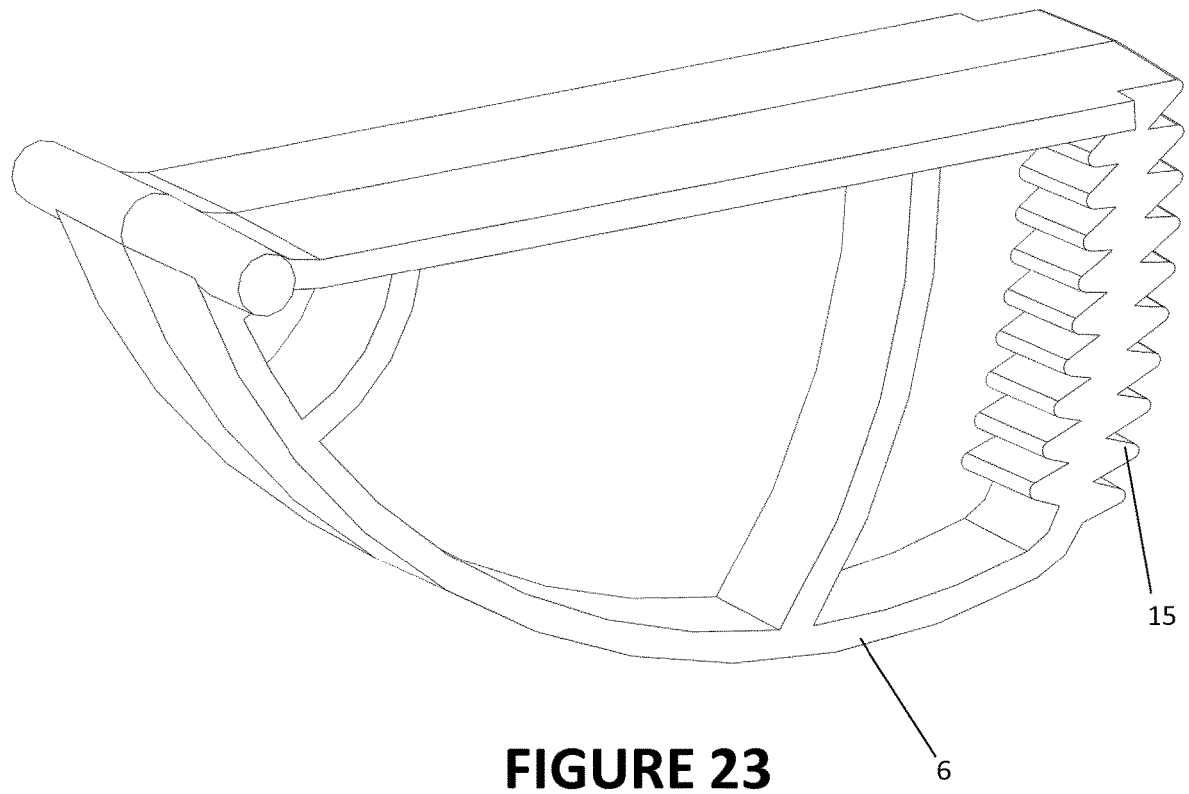
FIG. 23 is a perspective view illustrating the compression member shown in FIG. 17 in an exploded view, according to an embodiment.
Figure 24:
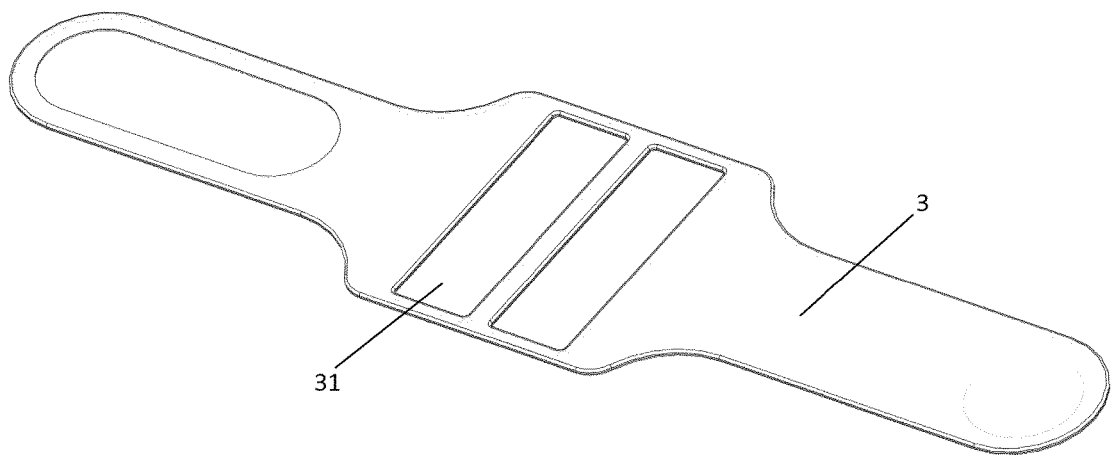
FIGS. 24-26 are perspective view illustrating a band forming a bracelet with different opening on the bracelet and including an opening for the frame, according to an embodiment.
Figure 25:
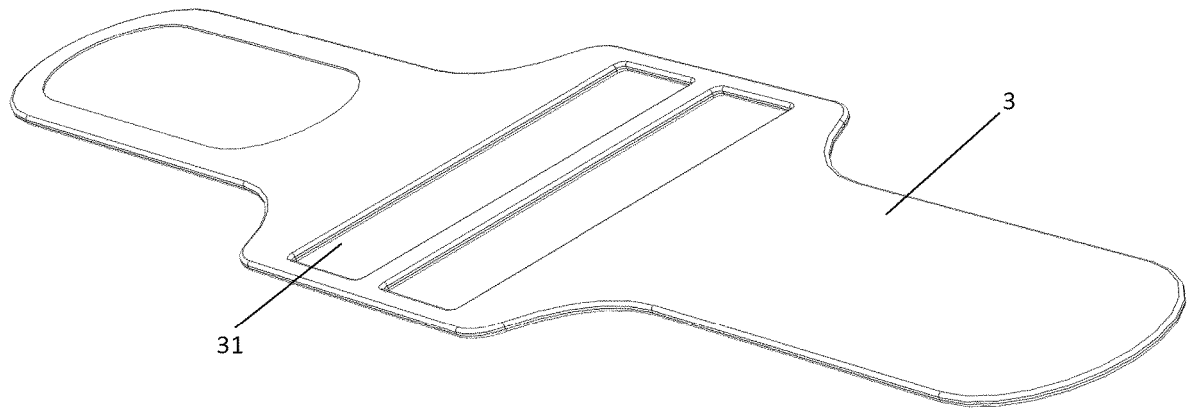
Figure 26:
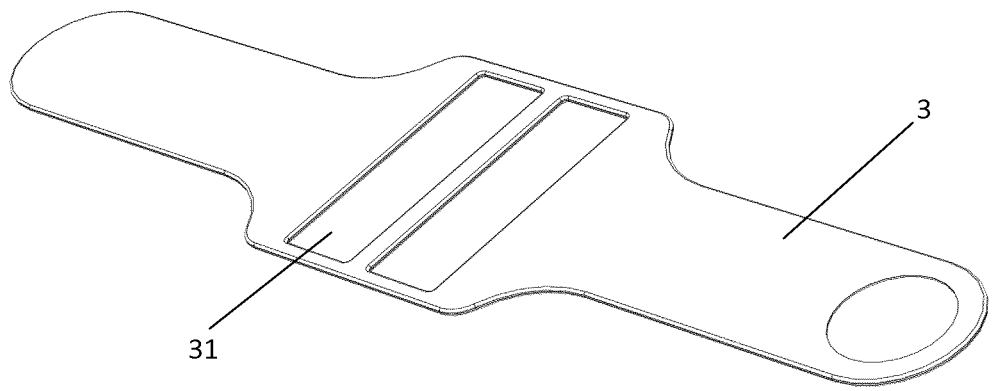
Figure 27:
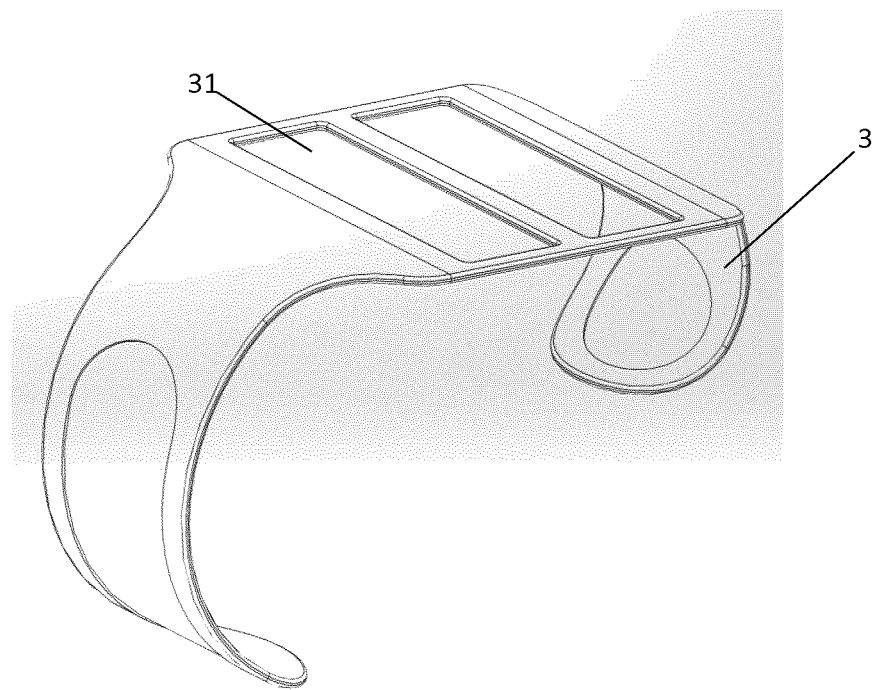
FIG. 27 is a perspective view illustrating the band shown in FIG. 24 deformed to form a bracelet, according to an embodiment.
Figure 28:
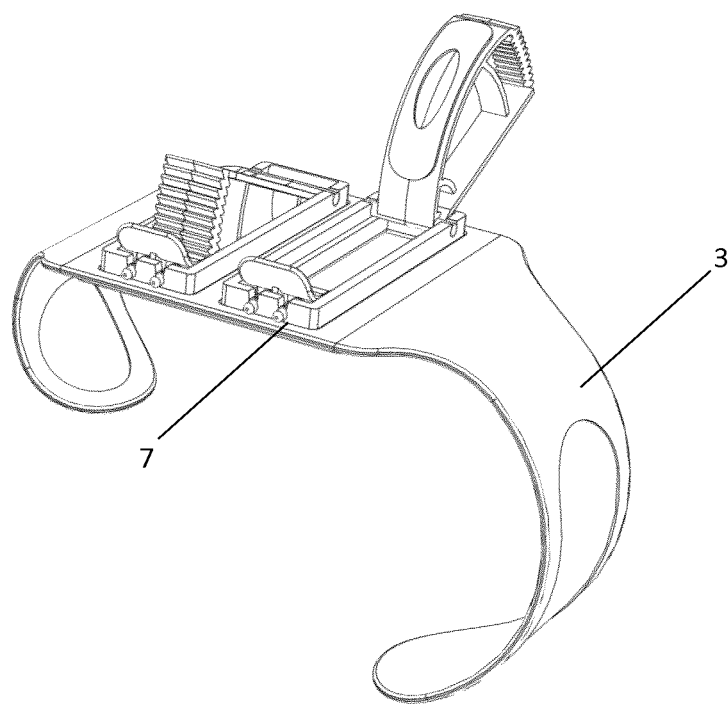
FIG. 28 is a perspective view illustrating a device for applying an adjustable and simultaneous compression on vessel access points, with the band of FIG. 27 as a bracelet, according to an embodiment.
Figure 29:
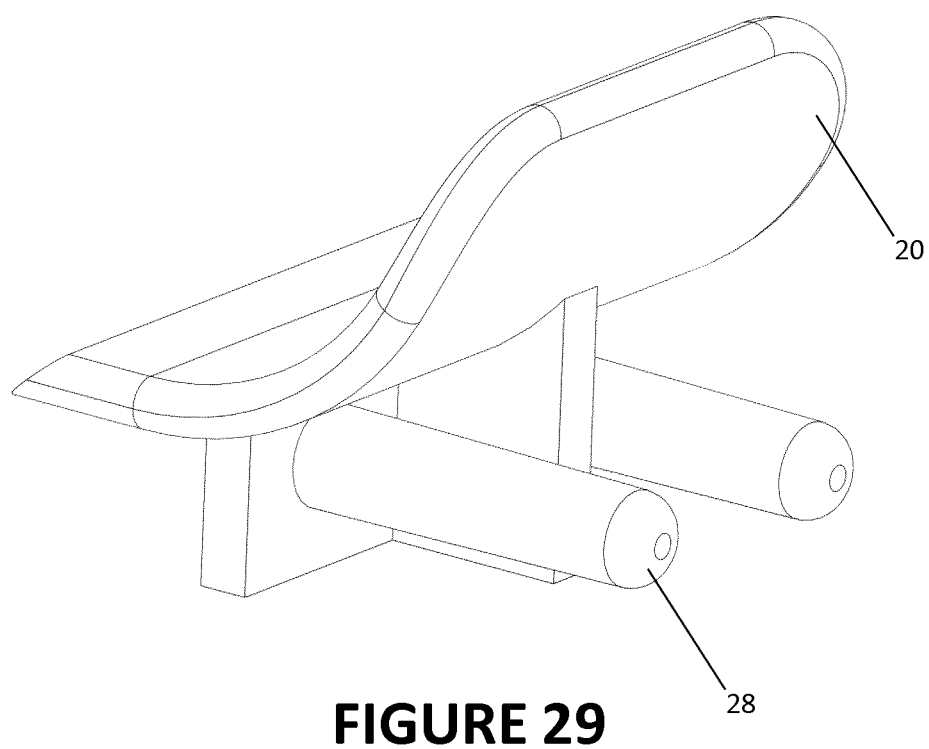
FIG. 29 is a perspective views illustrating the spring-loaded sliding button of FIGS. 18-19, according to an embodiment.

In FIGS. 18-29, and in particular in FIGS. 18-19 and 29, there is shown a ratchet mechanism comprising a spring-loaded sliding button 20, which is spring-loaded by a spring 29 (or more generally a biasing member loaded in compression or in tension). The spring 29 is held in place by a pin 28 which is rigid and receives the spring to press onto the spring-loaded sliding button 20, which is urged against the ratchet teeth 15 to hold them in place. The spring is held in place between walls 71, 72, the first one (71) belonging to the frame 7 and the second one (72) belonging to the spring-loaded sliding button 20, forming a cavity inside which the spring is compressed. The pin 28 is free to move thanks to an opening in the wall 71 through which it can travel.

The spring-loaded sliding button 20 comprises a portion for manipulation by a user (i.e., button), where the spring-loaded sliding button 20 can be pulled back away from the ratchet teeth by working against the spring to perform readjustments. This pull-back movement is shown in FIG. 19 (unlocked, spring-loaded sliding button 20 disengaged from the ratchet teeth), in comparison with FIG. 18 (locked, spring-loaded sliding button 20 engaged with the ratchet teeth) in which the spring-loaded sliding button 20 is pressed against the ratchet teeth 15 for locking. When the button is not pulled by the user, the spring compressed between walls 71, 72 pushes the spring-loaded sliding button 20 toward the ratchet teeth 15 again, for locking.

As shown in FIGS. 20-27, parts can be detachable from each other and, conversely, reassembled together. For example, the frame 7 is releasably insertable in the openings 31 and therefore detachable from the band 3. It means that the frame 7 and/or the band 3 can be independently sterilized and reused. The same applies to the compression member 6 which is releasably connected to the frame 7 (FIG. 20), e.g., the hinge point 9 can comprise an open hook which allows a hinge movement while allowing detachment of the compression member 6 from the frame 7. Again, it means that the frame 7 and/or the compression member 6 can be independently sterilized and reused. According to an embodiment, the soft pad 25 is detachable from the compression member 6 for disposal of the soft pad 25 and therefore, the compression member 6 can be independently sterilized and reused.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A device for applying an adjustable and simultaneous compression on vessel access points, the device comprising:
   a frame comprising a body with at least two cavities through the body to be placed about surfaces of a patient corresponding to the at least two cavities;
   at least two compression members to be movably fitted in the corresponding at least two cavities; and
   a pad along a bottom surface of each one of the at least two compression members;
   wherein, for each one compression member of the at least two compression members, a portion of the frame defines a space into which a portion of the compression member is fitted and around which the portion of the compression member hinges, a side of each one of the at least two compression members opposite a portion around which the portion of the compression member hinges comprising a locking mechanism which engages with the frame at an interface between said side and the frame to lock each one of the at least two compression members in a given hinge position for applying the adjustable and simultaneous compression by each one of the at least two compression members, each of the at least two compression members comprising a bottom surface having a constant radius of curvature along a bottom thereof to provide patient comfort during wearing; and
   wherein each pad comprises a hole forming a window for viewing through the pad.

2. The device of claim 1, wherein the locking mechanism comprises ratchet teeth which are asymmetrical to allow downward movement only.

3. The device of claim 2, wherein the side of each one of the at least two compression members comprising the teeth is curved with a constant radius of curvature therealong.

4. The device of claim 1, wherein the at least two compression members are made of a rigid material.

5. The device of claim 1, wherein the pad comprises a transparent portion forming a window for viewing through the pad.

6. The device of claim 1, wherein each of the at least two compression members is made of a transparent material for viewing therethrough.

7. The device of claim 1, wherein the at least two compression members comprise exactly two compression members.

8. The device of claim 1, wherein the frame has a bottom surface being curved along a width of the frame, to provide a shape of a portion of a cylinder to adapt to a shape of a body member.

9. The device of claim 1, further comprising a band forming a bracelet, wherein the frame is secured to the band.

10. The device of claim 9, wherein the band comprises an opening and the frame is insertable into the opening for securing the frame to the band, and releasable from the opening for detachment of the frame from the band.

11. A device for applying an adjustable compression on a vessel access point, the device comprising:
- a frame comprising a body forming a cavity to be placed on the vessel access point; and
- a compression member to be movably fitted in the cavity, wherein a portion of the frame defines a space into which a portion of the compression member is fitted and around which the portion of the compression member hinges, a side of the compression member opposite a portion around which the portion of the compression member hinges comprising teeth which engage with the frame at an interface between the teeth and the frame to lock the compression member in a given hinge position for applying the adjustable compression onto the vessel access point, the compression member comprising a bottom surface having a constant radius of curvature along a bottom thereof to provide patient comfort during wearing; and
- a pad along a bottom surface of the compression member, wherein the pad comprises a hole forming a window for viewing through the pad.

12. The device of claim 11, wherein the teeth are ratchet teeth which are asymmetrical to allow downward movement only.

13. The device of claim 11, wherein the side of the compression member comprising the teeth is curved with a constant radius of curvature therealong.

14. The device of claim 11, wherein the pad comprises an absorbent material which is impregnated by a pharmaceutically active substance.

15. The device of claim 11, wherein the compression member is made of a transparent material for viewing therethrough.

16. The device of claim 11, wherein at the interface between the teeth and the frame, the frame comprises a portion which is retracted for disengaging the teeth to hingeably move the compression member freely.

17. A device for applying an adjustable compression on a vessel access point, the device comprising:
- a frame comprising a body forming a cavity to be placed on the vessel access point; and
- a compression member to be movably fitted in the cavity, wherein a portion of the frame defines a space into which a portion of the compression member is fitted and around which the portion of the compression member hinges, a side of the compression member opposite a portion around which the portion of the compression member hinges comprising teeth which engage with the frame at an interface between the teeth and the frame to lock the compression member in a given hinge position for applying the adjustable compression onto the vessel access point, the compression member comprising a bottom surface having a constant radius of curvature along a bottom thereof to provide patient comfort during wearing,
wherein at the interface between the teeth and the frame, the frame comprises a portion which is retracted for disengaging the teeth to hingeably move the compression member freely.

* * * * *